(12) United States Patent
Naito

(10) Patent No.: US 10,165,932 B2
(45) Date of Patent: Jan. 1, 2019

(54) INSERTION DEVICE AND ROTATING TUBULAR MEMBER

(71) Applicant: OLYMPUS CORPORATION, Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/095,276

(22) Filed: Dec. 3, 2013

(65) Prior Publication Data
US 2014/0135578 A1 May 15, 2014

Related U.S. Application Data

(63) Continuation of application No. PCT/JP2013/050383, filed on Jan. 11, 2013.

(30) Foreign Application Priority Data

Mar. 29, 2012 (JP) .................................. 2012-076175

(51) Int. Cl.
*A61B 1/00* (2006.01)
*G02B 23/24* (2006.01)

(52) U.S. Cl.
CPC ........ *A61B 1/0016* (2013.01); *A61B 1/00156* (2013.01); *A61B 1/00158* (2013.01); *G02B 23/2476* (2013.01)

(58) Field of Classification Search
CPC .......................... A61B 1/0016; A61B 1/00156
USPC .......................................... 600/114, 128, 137
See application file for complete search history.

(56) References Cited

U.S. PATENT DOCUMENTS

| 8,500,628 B2 * | 8/2013 | Frassica et al. ............... 600/114 |
| 2005/0272976 A1 * | 12/2005 | Tanaka ............... A61B 1/00073 600/114 |

(Continued)

FOREIGN PATENT DOCUMENTS

| CN | 1933761 A | 3/2007 |
| EP | 2 668 888 A1 | 12/2013 |

(Continued)

OTHER PUBLICATIONS

International Search Report dated Apr. 23, 2013 issued in PCT/JP2013/050383.

(Continued)

*Primary Examiner* — Alexandra L Newton
*Assistant Examiner* — Rynae Boler
(74) *Attorney, Agent, or Firm* — Scully, Scott, Murphy & Presser, P.C.

(57) ABSTRACT

An insertion device includes a support member supporting a rotating tubular member between a base member and the rotating tubular member in diametrical directions and holding the rotating tubular member at a position where a rotation driving force is transmittable from a driving unit to an inner peripheral portion of the rotating tubular member connected to the driving unit. The insertion device includes a distal side ring member maintaining liquid-tightness between an outer peripheral portion of the base member and the inner peripheral portion of the rotating tubular member to a distal direction side of the driving unit placement cavity, and a proximal side ring member maintaining liquid-tightness between the outer peripheral portion of the base member and the inner peripheral portion of the rotating tubular member to a proximal direction side of the driving unit placement cavity.

13 Claims, 10 Drawing Sheets

(56) References Cited

U.S. PATENT DOCUMENTS

| | | |
|---|---|---|
| 2012/0002981 A1 | 1/2012 | Park |
| 2012/0004504 A1* | 1/2012 | Frassica et al. ............. 600/115 |
| 2012/0029281 A1 | 2/2012 | Frassica et al. |

FOREIGN PATENT DOCUMENTS

| | | |
|---|---|---|
| JP | 2006-034627 A | 2/2006 |
| JP | 2007-185394 A | 7/2007 |
| JP | 2008-540060 A | 11/2008 |
| JP | 2009-254554 A | 11/2009 |
| JP | 2010-527651 A | 8/2010 |
| JP | 2011-520562 A | 7/2011 |
| JP | 2011-520563 A | 7/2011 |

OTHER PUBLICATIONS

English Abstract only of WO2006125187 A2, dated Nov. 23, 2006.
English Abstract only of WO2009143077 A1, dated Nov. 26, 2009.
English Abstract only of WO2008144033 A2, dated Nov. 27, 2008.
English Abstract only of WO2009143069 A1, dated Jul. 21, 2011.
Extended Supplementary European Search Report dated Nov. 3, 2015 from related European Application No. 13 76 9004.6.
Translation of International Preliminary Report on Patentability together with the Written Opinion dated Oct. 9, 2014 received in related International Application No. PCT/JP2013/050383.
Chinese Office Action dated Jul. 3, 2015 from related Chinese Patent Application No. 201380003336.7, together with an English language translation.
Chinese Office Action dated Mar. 7, 2017 in Chinese Patent Application No. 201380003336.7.
Chinese Office Action dated Aug. 15, 2016 in related Chinese Patent Application No. 201380003336.7.
European Patent Office Communication dated Dec. 18, 2017 in corresponding European Application No. 13 769 004.6.
European Patent Office Communication dated Mar. 27, 2018 in corresponding European Application No. 13 769 004.6.

* cited by examiner

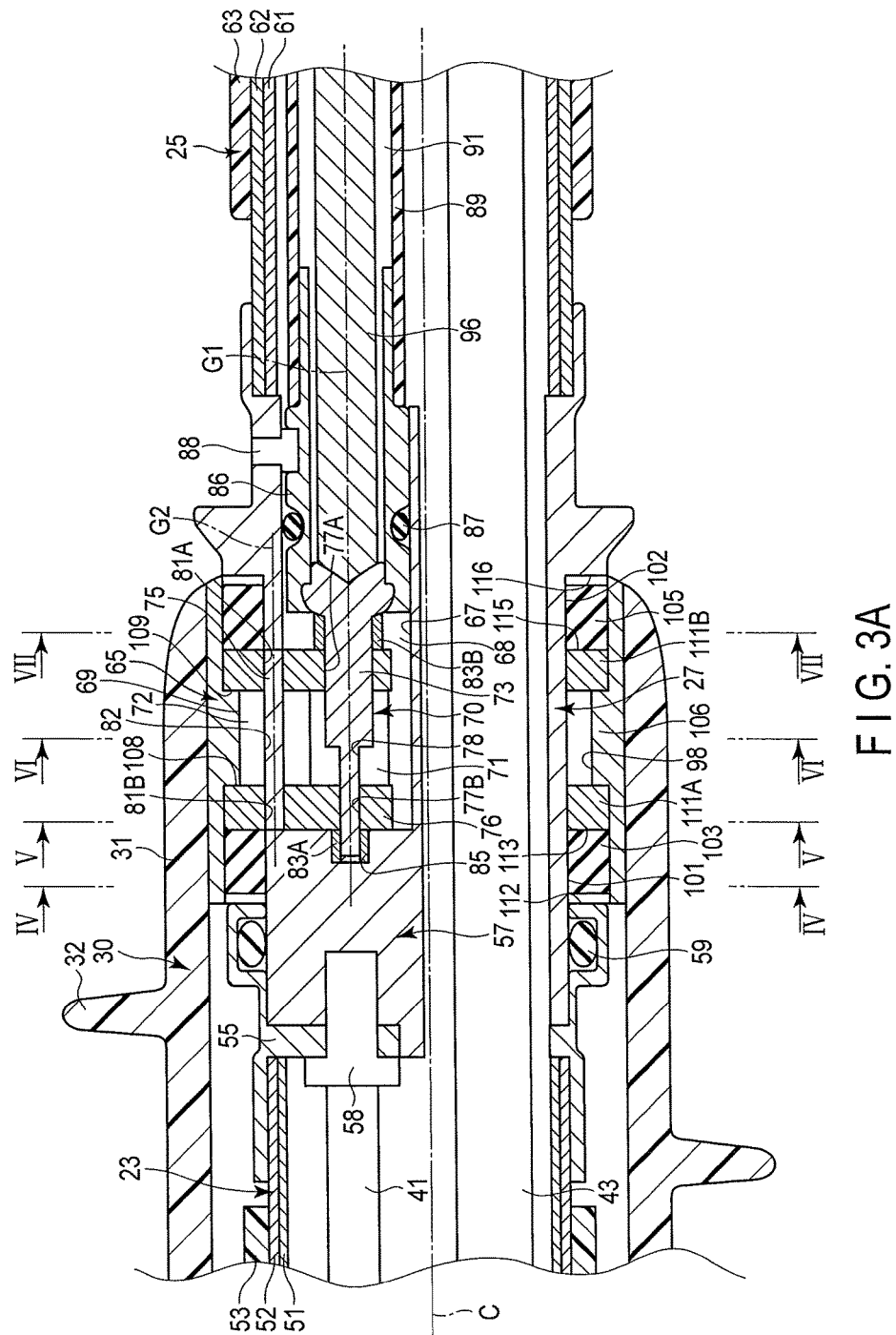
F I G. 3A

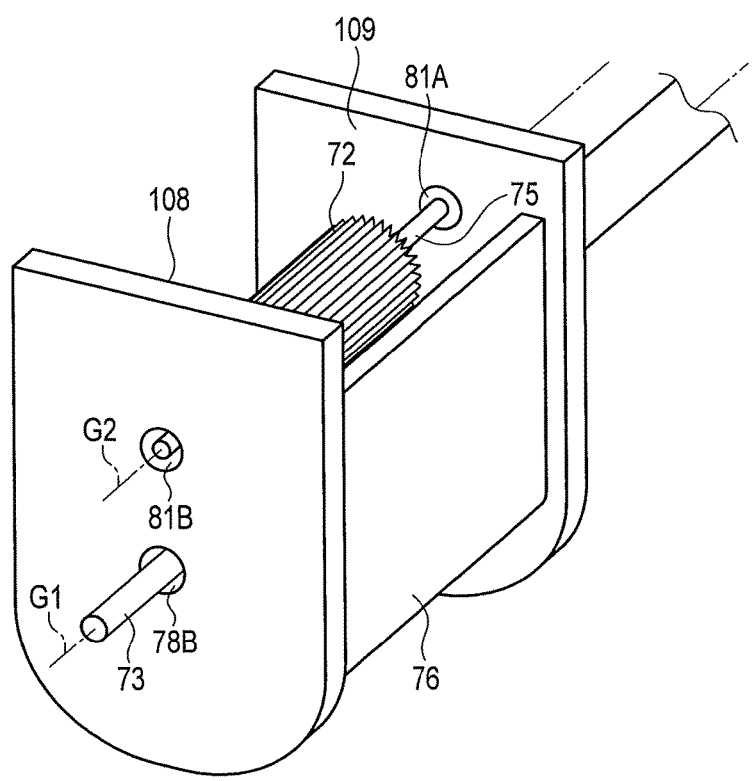
F I G. 8

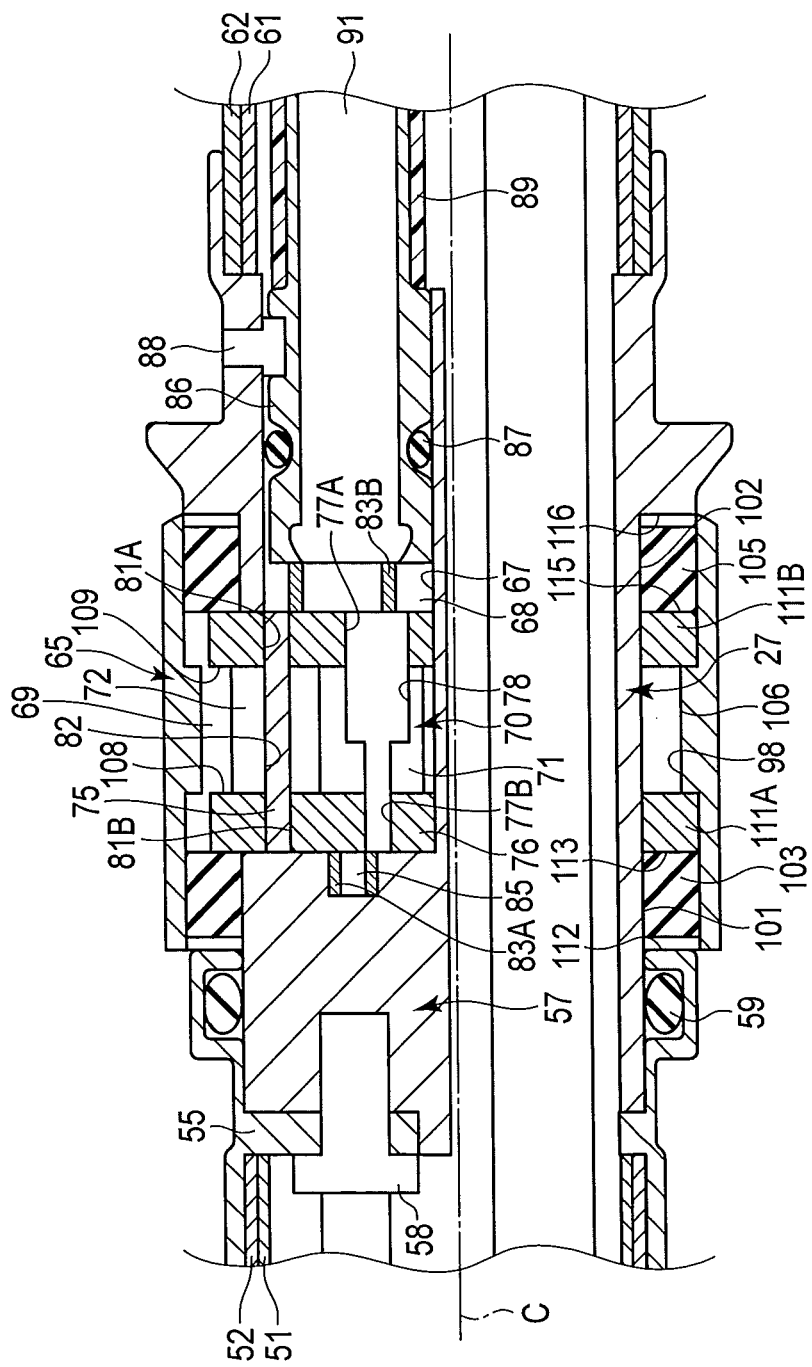
F I G. 9

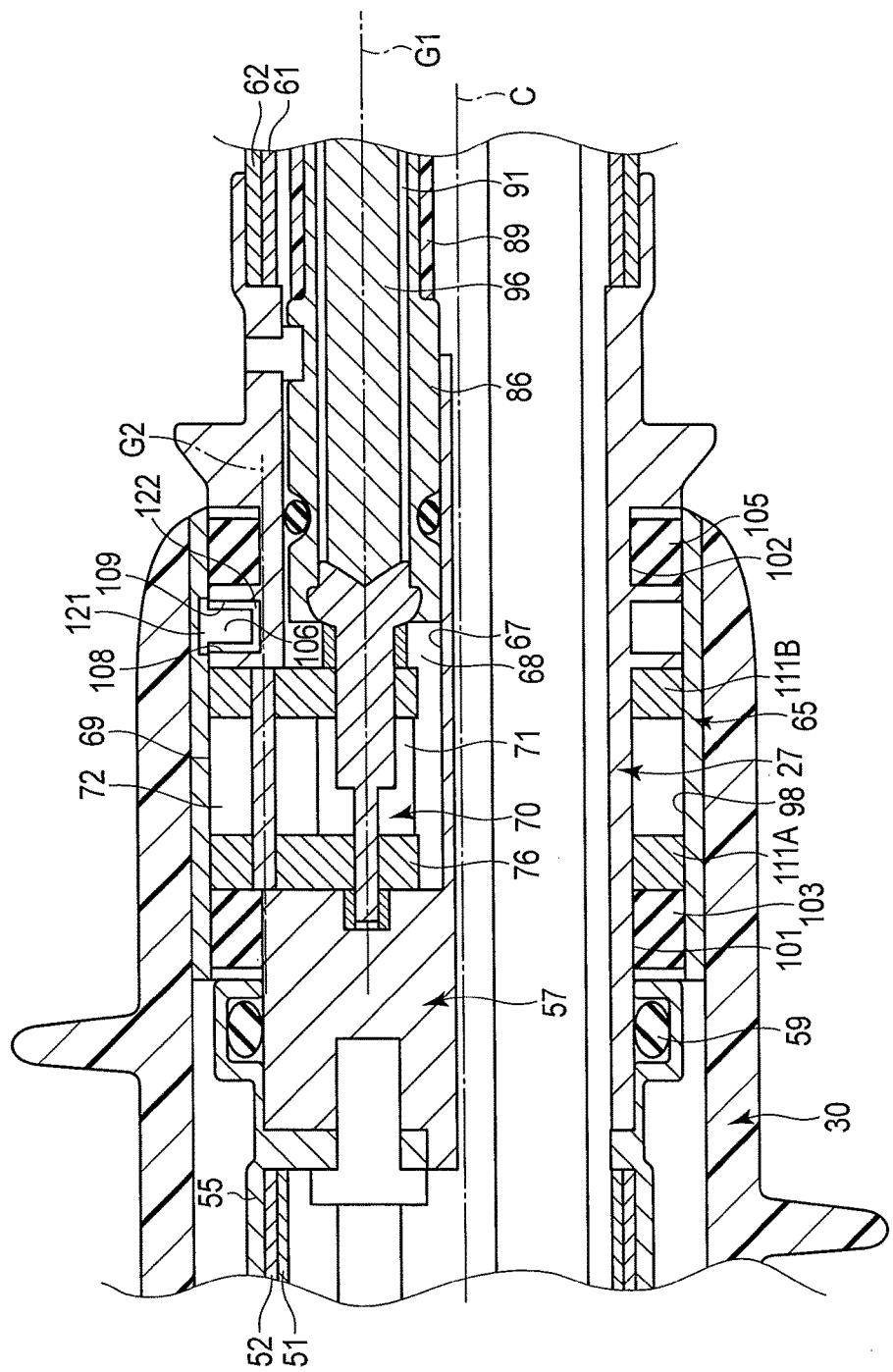
F I G. 10

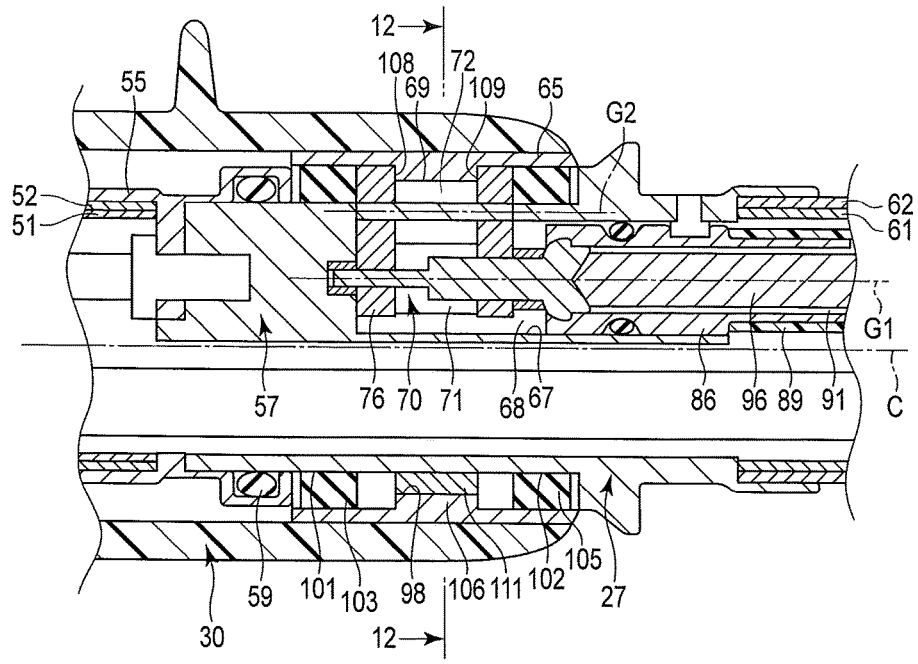
F I G. 11
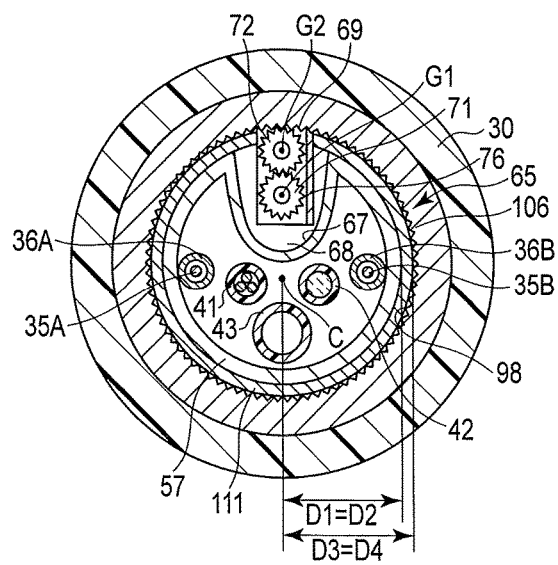
F I G. 12

INSERTION DEVICE AND ROTATING TUBULAR MEMBER

CROSS-REFERENCE TO RELATED APPLICATIONS

This is a Continuation application of PCT Application No. PCT/JP2013/050383, filed Jan. 11, 2013 and based upon and claiming the benefit of priority from prior Japanese Patent Application No. 2012-076175, filed Mar. 29, 2012, the entire contents of which are incorporated herein by reference.

BACKGROUND OF THE INVENTION

1. Field of the Invention

The present invention relates to an insertion device, and a rotating tubular member provided in (to) the insertion device. The insertion device includes an insertion section extending along a longitudinal axis, and the rotating tubular member which is rotatable relative to the insertion section in directions around the longitudinal axis.

2. Description of the Related Art

In an insertion device disclosed by one example in the specification of U.S. Patent Application Publication No. 2012/002981, a rotating tubular member rotatable relative to an insertion section in directions around a longitudinal axis is attached to the insertion section extending along the longitudinal axis. In this insertion device, a driving shaft which is a linear member extends through an inside of the insertion section along the longitudinal axis. A distal end of the driving shaft is connected to a driving unit. The driving unit includes a first gear to which the driving shaft is coupled, and a second gear which is toothed with the first gear. When a driving force is transmitted via the driving shaft, each of the first gear and the second gear rotates around a corresponding gear axis, and the driving unit is driven. The rotating tubular member is provided with an inner peripheral gear portion which is toothed with the second gear. When the driving unit is driven, the rotating tubular member rotates relative to the insertion section in one of the directions around the longitudinal axis.

The insertion portion includes a proximal side base member, and a distal side base member coupled to the distal direction side of the proximal side base member. A driving unit placement cavity in which the driving unit is disposed is defined by the proximal side base member and the distal side base member. The driving unit placement cavity is open with respect to an outside of the insertion section through an opening. A proximal side seal ring which is a proximal side ring member is provided on an outer peripheral portion of the proximal side base member. The proximal side seal ring is located to the proximal direction side of the opening of the driving unit placement cavity. A distal side seal ring which is a distal side ring member is provided on an outer peripheral portion of the distal side base member. The distal side seal ring is located to the distal direction side of the opening of the driving unit placement cavity. The proximal side seal ring maintains liquid-tightness between the outer peripheral portion of the proximal side base member and an inner peripheral portion of the rotating tubular member. The distal side seal ring maintains liquid-tightness between the outer peripheral portion of the distal side base member and the inner peripheral portion of the rotating tubular member. Therefore, the proximal side seal ring and the distal side seal ring prevent liquid inflow from the outside of the insertion section into the driving unit placement cavity, and prevent the driving unit from, for example, being damaged by a liquid.

BRIEF SUMMARY OF THE INVENTION

According to one aspect of the invention, an insertion device includes that: an insertion section which extends along a longitudinal axis with the longitudinal axis being an axial center; a rotating tubular member which is disposed to cover an outer peripheral of the insertion section; a driving unit which is configured to be driven to rotate the rotating tubular member relative to the insertion section in one of directions around the longitudinal axis; a base member which is integrally formed in a part of the insertion section, and which defines a driving unit placement cavity to dispose the driving unit; a support member which is configured to support the rotating tubular member between the base member and the rotating tubular member in diametrical directions, and which is configured to hold the rotating tubular member at a position where a rotation driving force is transmittable from the driving unit to an inner peripheral portion of the rotating tubular member connected to the driving unit; a distal side ring member which is configured to maintain liquid-tightness between an outer peripheral portion of the base member and the inner peripheral portion of the rotating tubular member in a part to a distal direction side of the driving unit placement cavity, and thereby which is configured to prevent liquid inflow from the distal direction side into the driving unit placement cavity; and a proximal side ring member which is configured to maintain liquid-tightness between the outer peripheral portion of the base member and the inner peripheral portion of the rotating tubular member in a part to a proximal direction side of the driving unit placement cavity, and thereby which is configured to prevent liquid inflow from the proximal direction side into the driving unit placement cavity.

According to one another aspect of the invention, s rotating tubular member in an insertion device, the insertion device including an insertion section which extends along a longitudinal axis with the longitudinal axis being an axial center, and a driving unit which is configured to be driven, the rotating tubular member being disposed to cover an outer peripheral of the insertion section and being configured to rotate relative to the insertion section in one of directions around the longitudinal axis when the driving unit is driven, wherein the rotating tubular member is attached to the insertion section in which a base member is integrally formed, the base member defining a driving unit placement cavity to dispose the driving unit, the rotating tubular member is configured to be supported by a support member at a position where a rotation driving force is transmittable from the driving unit to an inner peripheral portion of the rotating tubular member connected to the driving unit, the support member being provided between the base member and the rotating tubular member in diametrical directions, liquid inflow from the distal direction side into the driving unit placement cavity is prevented by a distal side ring member, the distal side ring member being configured to maintain liquid-tightness between an outer peripheral portion of the base member and the inner peripheral portion of the rotating tubular member in a part to a distal direction side of the driving unit placement cavity, and liquid inflow from the proximal direction side into the driving unit placement cavity is prevented by a proximal side ring member, the proximal side ring member being configured to maintain liquid-tightness between the outer peripheral portion of the base member and the inner peripheral portion of the rotating tubular member in a part to a proximal direction side of the driving unit placement cavity.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a schematic sectional view showing a configuration of a second intermediary connection section of an insertion section according to the first embodiment;

FIG. 8 is a schematic perspective view showing a driving unit and a frame member according to the first embodiment;

FIG. 9 is a schematic sectional view showing the second intermediary connection section of the insertion section according to the first embodiment when a driving shaft is not connected to the driving unit;

FIG. 10 is a schematic sectional view showing a configuration of the second intermediary connection section of the insertion section according to a first modification;

FIG. 11 is a schematic sectional view showing a configuration of the second intermediary connection section of the insertion section according to a second modification; and FIG. 12 is a sectional view taken along the line 12-12 in FIG. 11.

DETAILED DESCRIPTION OF THE INVENTION

First Embodiment

Figure 1:
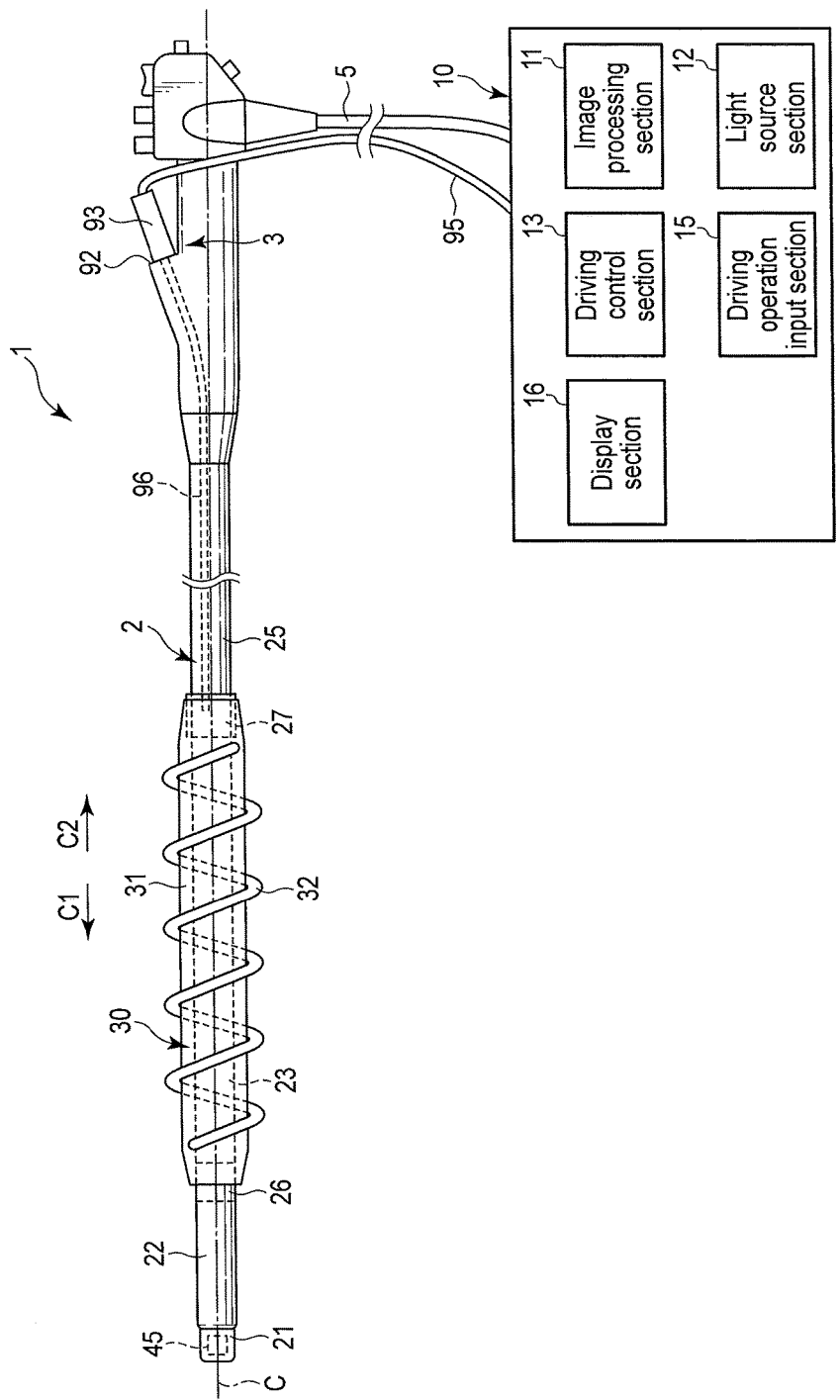
FIG. 1 is a schematic diagram showing an endoscope device according to a first embodiment of the present invention.

A first embodiment of the present invention is described with reference to FIG. 1 to FIG. 9. FIG. 1 is a diagram showing an endoscope device (endoscopic device) 1 which is an insertion device according to the first embodiment. As shown in FIG. 1, the endoscope device 1 includes an insertion section (endoscope insertion section) 2 extending along a longitudinal axis C, and an operation section (endoscope operation section) 3 provided to a proximal direction side of the insertion section 2. An axial center of the insertion section 2 is the longitudinal axis C, and the insertion is configured to be inserted into a body cavity when the endoscope device 1 is used. One end of a universal cable 5 is connected to the operation section 3. The other end of the universal cable 5 is connected to a peripheral unit 10. The peripheral unit 10 includes an image processing section 11, a light source section 12, a driving control section 13, a driving operation input section 15, and a display section 16. It is to be noted that one of the directions parallel to the longitudinal axis C is a distal direction (direction of an arrow C1 in FIG. 1), and the direction opposite to the distal direction is a proximal direction (direction of an arrow C2 in FIG. 1).

The insertion section 2 includes a distal hard section 21 provided on the most distal direction side, a bending section 22 provided to the proximal direction side of the distal hard section 21, a first flexible tube section 23 provided to the proximal direction side of the bending section 22, and a second flexible tube section 25 provided to the proximal direction side of the first flexible tube section 23. The bending section 22 and the first flexible tube section 23 are connected by a first intermediary connection section 26. The first flexible tube section 23 and the second flexible tube section 25 are connected by a second intermediary connection section 27.

A tube member 30 is provided to an outer peripheral direction side of the insertion section 2. The insertion section 2 is inserted through the tube member 30. The tube member 30 extends along the longitudinal axis C between the first intermediary connection section 26 and the second intermediary connection section 27. The tube member 30 is rotatable relative to the insertion section 2 in directions around the longitudinal axis. The tube member 30 includes a tube body 31, and a fin 32 spirally extending on an outer peripheral portion of the tube body 31 along the longitudinal axis C.

Figure 2:
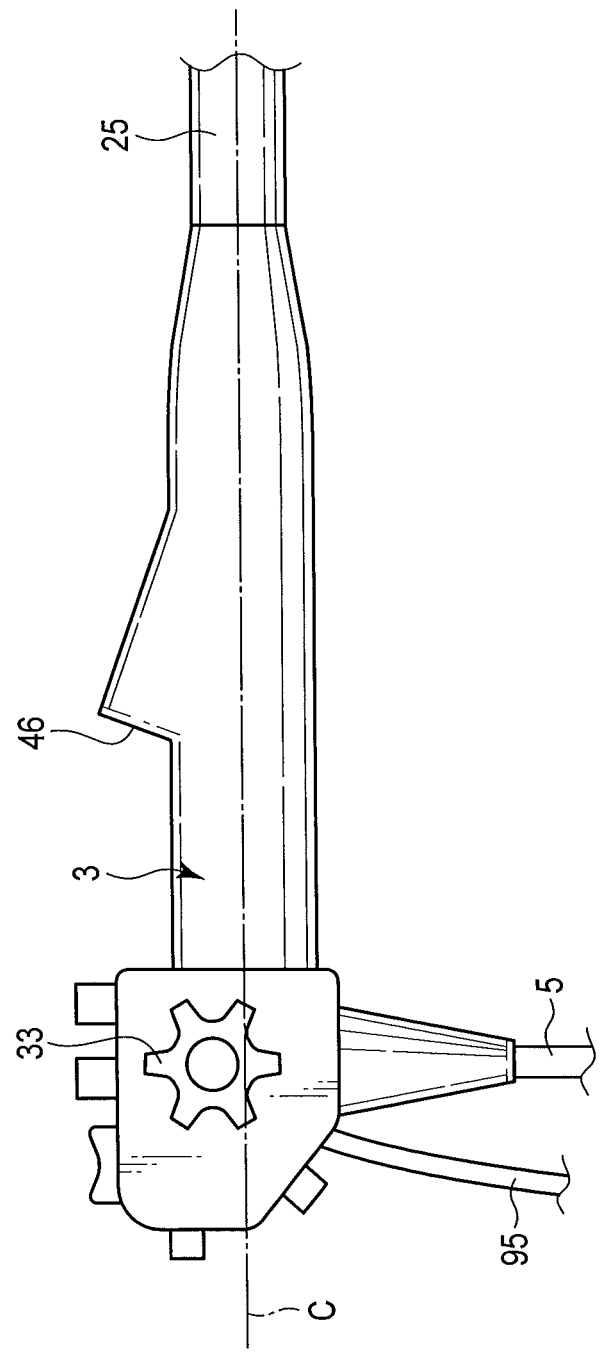
FIG. 2 is a schematic diagram showing a side surface of an operation section of the endoscope device according to the first embodiment opposite to a side surface shown in FIG. 1.
Figure 3B:
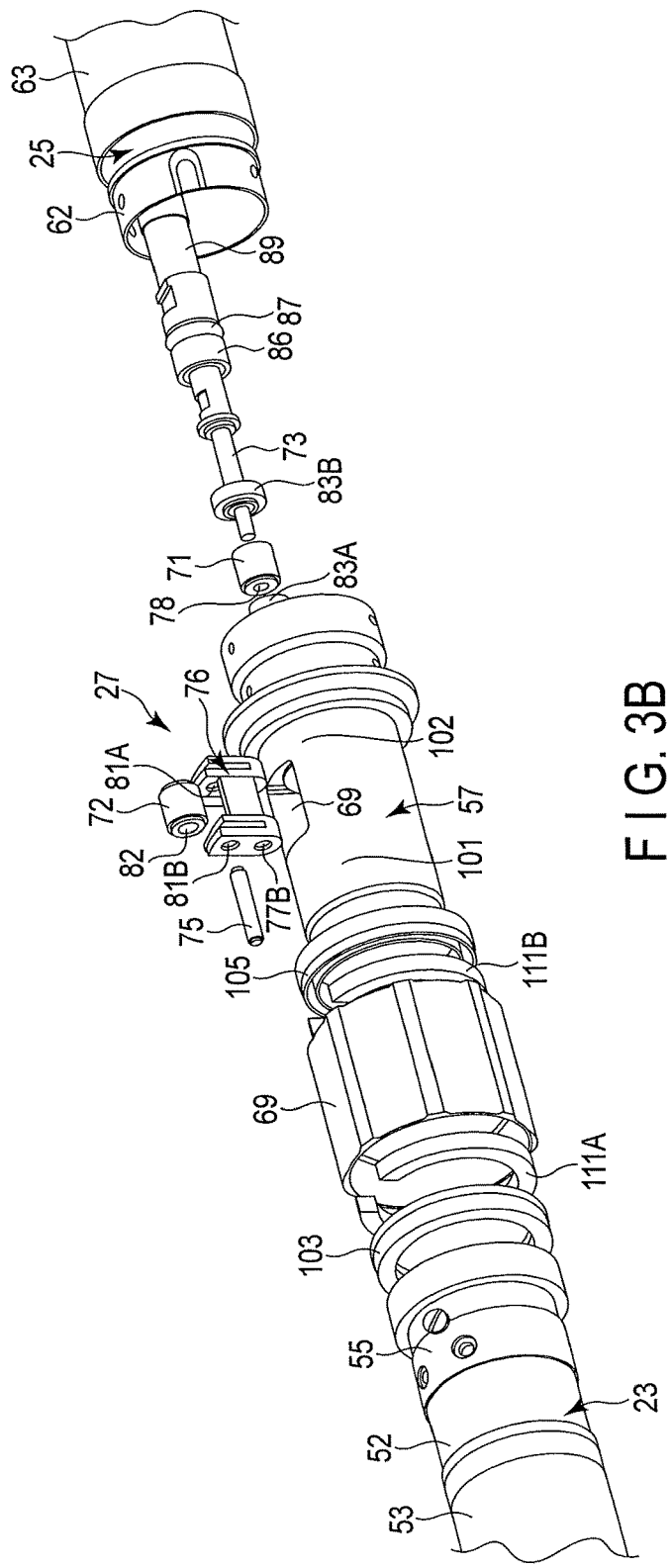
FIG. 3B is a schematic perspective view showing the configuration of the second intermediary connection section of the insertion section according to the first embodiment that is disjoined into members.
Figure 4:
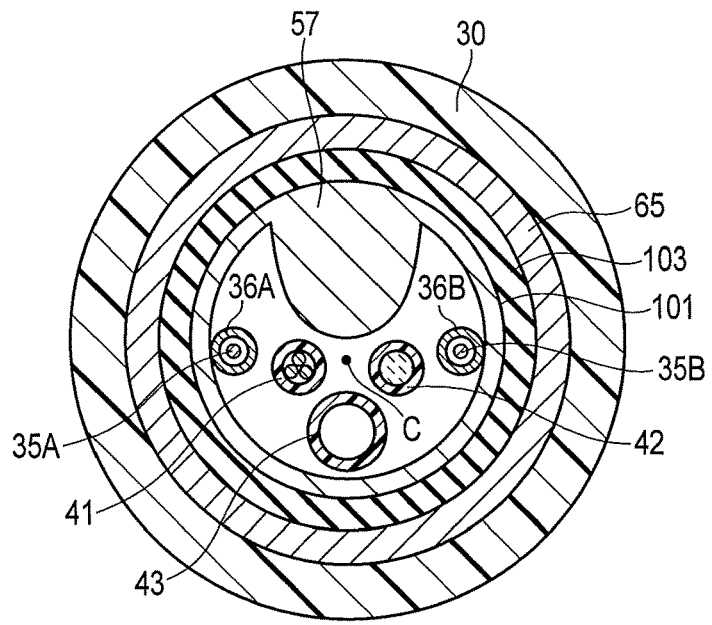
FIG. 4 is a sectional view taken along the line IV-IV in FIG. 3A.
Figure 5:
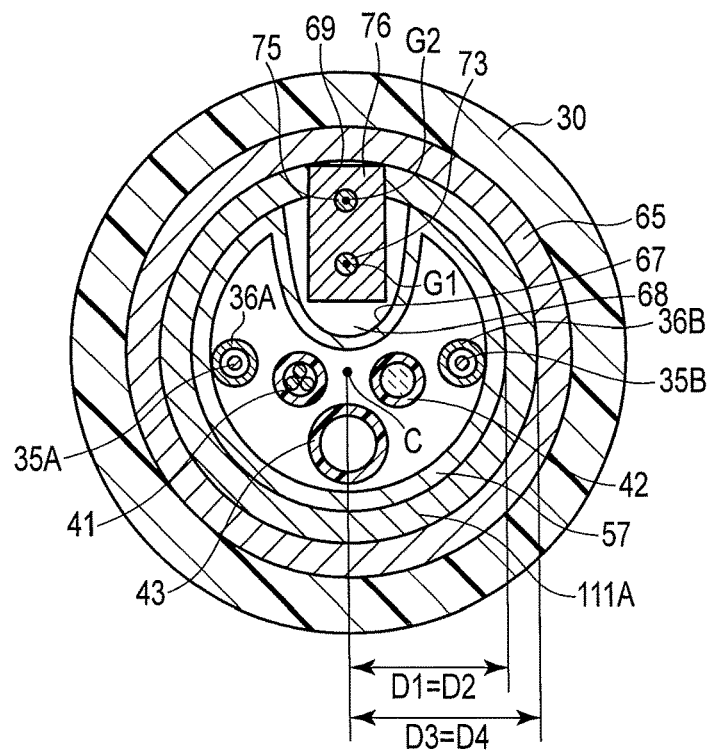
FIG. 5 is a sectional view taken along the line V-V in FIG. 3A.
Figure 6:
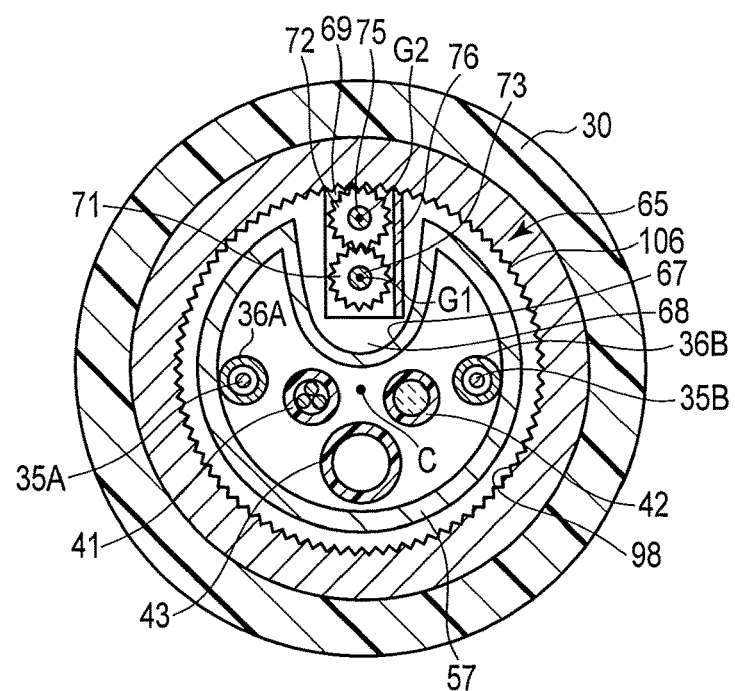
FIG. 6 is a sectional view taken along the line VI-VI in FIG. 3A.
Figure 7:
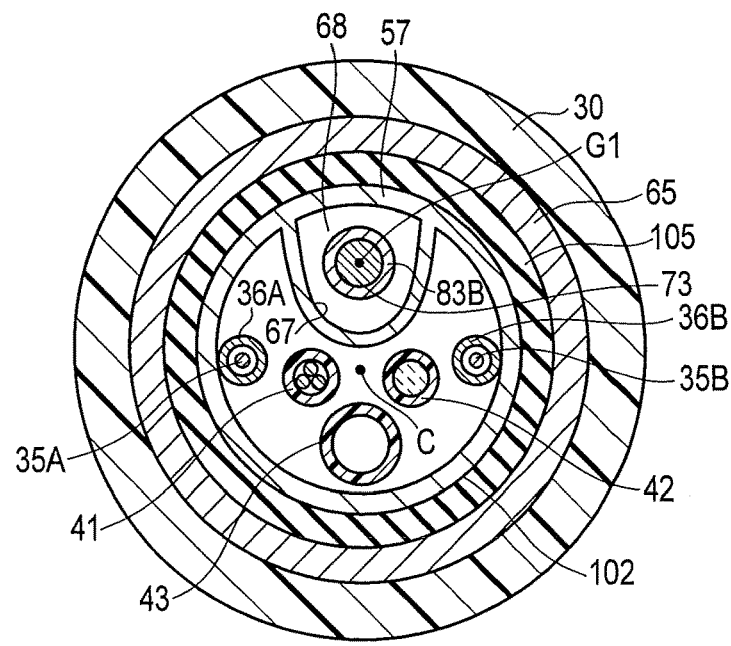
FIG. 7 is a sectional view taken along the line VII-VII in FIG. 3A.

FIG. 2 is a diagram showing a side surface of the operation section 3 opposite to a side surface shown in FIG. 1. As shown in FIG. 2, a bending operation knob 33 which is a bending operation input section configured to input a bending operation of the bending section 22 is provided on an outer surface of the operation section 3. FIG. 3A and FIG. 3B are diagrams showing the configuration of the second intermediary connection section 27. FIG. 4 is a sectional view taken along the line IV-IV in FIG. 3A. FIG. 5 is a sectional view taken along the line V-V in FIG. 3A. FIG. 6 is a sectional view taken along the line VI-VI in FIG. 3A. FIG. 7 is a sectional view taken along the line VII-VII in FIG. 3A. As shown in FIG. 4 and FIG. 7, bending wires 35A and 35B extend through an inside of the insertion section 2 along the longitudinal axis C. Proximal ends of the bending wires 35A and 35B are connected to the bending operation knob 33 inside the operation section 3. Distal ends of the bending wires 35A and 35B are connected to a distal portion of the bending section 22. In response to the bending operation of the bending operation knob 33, the bending wire 35A or the bending wire 35B is pulled, and the bending section 22 bends.

Each of the bending wires 35A and 35B is inserted through a corresponding coil 36A or 36B. Proximal ends of the coils 36A and 36B are fixed to an inner peripheral portion of the operation section 3. Distal ends of the coils 36A and 36B are connected to an inner peripheral portion of the first intermediary connection section 26. In the present embodiment, the two bending wires 35A and 35B are provided, and the bending section 22 is bendable in two directions. However, for example, four bending wires may be provided, and the bending section 22 may be bendable in four directions.

As shown in FIG. 3A to FIG. 7, an imaging cable 41, a light guide 42, and a treatment tool channel tube 43 extend through the inside of the insertion section 2 along the longitudinal axis C. As shown in FIG. 1, an image pickup element 45 configured to image a subject is provided inside the distal hard section 21 (the distal portion of the insertion section 2). A distal end of the imaging cable 41 is connected to the image pickup element 45. The imaging cable 41 extends through the inside of the insertion section 2, the inside of the operation section 3, and an inside of the universal cable 5, and has its proximal end connected to the image processing section 11 of the peripheral unit 10. A subject image (subject picture) processed by the image processing section 11 is displayed on the display section 16. The light guide 42 extends through the inside of the insertion section 2, the inside of the operation section 3, and the inside of the universal cable 5, and has its proximal end connected to the light source section 12 of the peripheral unit 10. Light emitted from the light source section 12 is guided by the light guide 42, and applied to the subject from the distal portion (distal hard section 21) of the insertion section 2.

As shown in FIG. 2, a treatment tool insertion portion 46 into which a treatment tool such as a forceps is inserted is provided on the outer surface of the operation section 3. The treatment tool channel tube 43 has its proximal end connected to the treatment tool insertion portion 46 and extends through the inside of the insertion section 2 and the inside of the operation section 3. The treatment tool inserted from the treatment tool insertion portion 46 projects toward the distal direction from an opening (not shown) of the distal hard section 21 through an inside of the treatment tool channel tube 43. A treatment is then conducted by the treatment tool in a state that the treatment tool projects from the opening of the distal hard section 21.

As shown in FIG. 3A, a metallic first helical tube (first flex) 51 is provided in the first flexible tube section 23. A part to the outer peripheral direction side of the first helical tube (first spiral tube) 51 is covered with a metallic first flexible reticular tube (first flexible braid) 52. A part to the outer peripheral direction side of the first flexible reticular tube (first flexible mesh tube) 52 is covered with a resin first flexible envelope 53. A proximal end of the first helical tube 51 and a proximal end of the first flexible mesh tube 52 are fitted in an intermediary member 55. The second intermediary connection section 27 includes a metallic base member 57. The intermediary member 55 is fitted in the base member 57 via a ring member 59. The intermediary member 55 is attached to the base member 57 via a screw 58. In this way, the first flexible tube section 23 is coupled to the second intermediary connection section 27.

A metallic second helical tube (second flex) 61 is provided in the second flexible tube section 25. A part to the outer peripheral direction side of the second helical tube (second spiral tube) 61 is covered with a metallic second flexible reticular tube (second flexible braid) 62. A part to the outer peripheral direction side of the second flexible reticular tube (second flexible mesh tube) 62 is covered with a resin second flexible envelope 63. A distal end of the second helical tube 61 and a distal end of the second flexible mesh tube 62 are fitted in the base member 57. In this way, the second flexible tube section 25 is coupled to the second intermediary connection section 27.

A rotating tubular member 65 is attached to the second intermediary connection section 27 of the insertion section 2 so that the insertion section 2 is inserted therethrough. The rotating tubular member 65 is rotatable relative to the insertion section 2 in the directions around the longitudinal axis. The proximal portion of the tube member 30 is in close contact with an outer peripheral portion of the rotating tubular member 65. Thus, the tube member 30 is fixed to the rotating tubular member 65, and the tube member 30 is rotatable in the directions around the longitudinal axis together with the rotating tubular member 65. The distal portion of the tube member 30 is in contact with an outer peripheral portion of the first intermediary connection section 26 movably relative to the insertion portion 2 in the directions around the longitudinal axis.

The base member 57 is formed into integral one from a single member. Since the base member 57 is a part of the insertion section 2, the longitudinal axis C is the axial center. A driving unit 70 is disposed in the second intermediary connection section 27. When driven, the driving unit 70 rotates the rotating tubular member 65 relative to the insertion section 2. The driving unit 70 is disposed in a driving unit placement cavity 68 defined by a cavity defining portion 67 of the base member 57. The driving unit placement cavity 68 is open to an outside of the insertion section 2 through an opening 69.

As shown in FIG. 3A, the driving unit 70 includes a first gear 71, and a second gear 72 which is provided to the outer peripheral direction side of the first gear 71. The first gear 71 is toothed with the second gear 72. A gear axis G1 of the first gear 71 is defined by a first shaft member 73. A gear axis G2 of the second gear 72 is defined by a second shaft member 75.

A substantially U-shaped frame member 76 attached to the driving unit 70 is disposed in the driving unit placement cavity 68. FIG. 8 is a diagram showing the configurations of the driving unit 70 and the frame member 76. As shown in FIG. 3A, FIG. 3B, and FIG. 8, the driving unit 70 is disposed inside the frame member 76. Bore portions (hole portions) 77A and 77B are formed in the frame member 76 along the gear axis G1 of the first gear 71. A bore portion (hole portion) 78 is formed in the first gear 71 along the gear axis G1. When the first shaft member 73 is inserted through the bore portions 77A, 77B, and 78, the first gear 71 is attached to the frame member 76. The first gear 71 and the first shaft member 73 are rotatable together relative to the frame member 76 around the gear axis G1.

Bore portions (hole portions) 81A and 81B are formed in the frame member 76 with the gear axis G2 of the second gear 72 being center. A bore portion (hole portion) 82 is formed in the second gear 72 along the gear axis G2. When the second shaft member 75 is inserted through the bore portion 82 and inserted in the bore portions 81A and 81B, the second gear 72 is attached to the frame member 76. The second gear 72 and the second shaft member 75 are rotatable together relative to the frame member 76 around the gear axis G2.

An engagement slot (engagement groove) 85 is formed in the base member 57. A ring member 83A is fixed to the engagement slot 85. A ring member 83B is provided to the proximal direction side of the frame member 76. When the first shaft member 73 is inserted through the ring member 83B and engaged with the ring member 83A, the driving unit 70 (first gear 71) is attached to the base member 57. When the first shaft member 73 is engaged with the ring member 83A in a state that the first shaft member 73 is inserted through the bore portions 77A, 77B, and 78, the frame member 76 is fixed to the base member 57.

As shown in FIG. 3A, a metallic connection pipe 86 is fixed to the cavity defining portion 67 of the base member 57 via a ring member 87 and a screw 88. A distal end of a member channel tube 89 is connected to the connection pipe 86. The member channel tube 89 extends through an inside of the second flexible tube section 25 of the insertion section 2 along the longitudinal axis C. A member channel 91 is formed inside the connection pipe 86 and the member channel tube 89. A distal end of the member channel 91 is in communication with the driving unit placement cavity 68.

As shown in FIG. 1, a member insertion portion 92 is provided on the outer surface of the operation section 3. The member channel tube 89 has its proximal end connected to the member insertion portion 92 and extends through the inside of the second flexible tube section 25 and the inside of the operation section 3. Therefore, the member channel 91 extends from the member insertion portion 92 up to the driving unit placement cavity 68 through the inside of the member channel tube 89.

A motor 93 which is a driving member is attached to the member insertion portion 92. One end of a motor cable 95 is connected to the motor 93. The other end of the motor cable 95 is connected to the driving control section 13 of the peripheral unit 10.

As shown in FIG. 1 and to FIG. 3A, the motor 93 is connected to the driving unit 70 via a driving shaft 96 which is a linear member. The driving shaft 96 extends along the member channel 91. That is, the driving shaft 96 extends through the inside of the second flexible tube section 25 of the insertion section 2 along the longitudinal axis C. The first shaft member 73 is coupled to a distal portion of the driving shaft 96.

If the motor 93 is driven by the operation in the driving operation input section 15, the driving shaft 96 rotates around the gear axis G1. Then the first gear 71 rotates around the gear axis G1, and the second gear 72 rotates around the gear axis G2. That is, if the driving force from the motor 93 is transmitted to the driving unit 70 via the driving shaft 96, the driving unit 70 is driven.

As shown in FIG. 3A and to FIG. 6, an inner peripheral gear portion 98 which is toothed with the second gear 72 is provided on an inner peripheral portion of the rotating tubular member 65. The inner peripheral gear portion 98 is provided over all-round of the rotating tubular member 65 in the directions around the longitudinal axis. Thus, when the second gear 72 rotates around the gear axis G2, the rotating tubular member 65 rotates in one of the directions around the longitudinal axis. That is, the inner peripheral gear portion 98 serves as a driving force receiving portion which is connected to the driving unit 70 and to which a rotation driving force to rotate the rotating tubular member 65 is transmitted when the driving unit 70 is driven. The second gear 72 and the inner peripheral gear portion 98 are toothed with each other at the opening 69 of the driving unit placement cavity 68.

As shown in FIG. 3A and to FIG. 4, a distal side circular surface 101 is provided on the outer peripheral portion of the base member 57 with being located to the distal direction side of the opening 69 of the driving unit placement cavity 68. The distal side circular surface 101 is formed into the shape of a circular surface around the longitudinal axis C. As shown in FIG. 3A and to FIG. 7, a proximal side circular surface 102 is provided to the proximal direction side of the opening 69 of the driving unit placement cavity 68. The proximal side circular surface 102 is formed into the shape of a circular surface around the longitudinal axis C.

A distal side seal ring 103 which is a distal side ring member is provided on the distal side circular surface 101. The distal side seal ring 103 maintains liquid-tightness between the distal side circular surface 101 and the inner peripheral portion of the rotating tubular member 65. A proximal side seal ring 105 which is a proximal side ring member is provided on the proximal side circular surface 102. The proximal side seal ring 105 maintains liquid-tightness between the proximal side circular surface 102 and the inner peripheral portion of the rotating tubular member 65. Therefore, the distal side seal ring 103 and the proximal side seal ring 105 prevent liquid inflow from the outside of the insertion section 2 into the driving unit placement cavity 68. Here, the center of the distal side circular surface 101 is the longitudinal axis C, so that the distal side seal ring 103 is disposed coaxially with the longitudinal axis C. Similarly, the center of the proximal side circular surface 102 is the longitudinal axis C, so that the proximal side seal ring 105 is disposed coaxially with the longitudinal axis C.

The rotating tubular member 65 includes a protrusion 106 projecting toward an inner peripheral direction. The protrusion 106 is formed integrally with the rotating tubular member 65. The protrusion 106 is located between the distal side seal ring 103 and the proximal side seal ring 105 in directions parallel to the longitudinal axis C. The protrusion 106 is provided with the inner peripheral gear portion 98. Therefore, the protrusion 106 is inserted in the frame member 76 from the opening 69 of the driving unit placement cavity 68.

The frame member 76 is provided with a distal side abutment portion 108 and a proximal side abutment portion 109 on which the protrusion 106 of the rotating tubular member 65 can abut (is abutable). Since the frame member 76 is fixed to the base member 57, the distal side abutment portion 108 and the proximal side abutment portion 109 are provided to be fixed to the base member 57. When the protrusion 106 abuts on the distal side abutment portion 108, the movement of the rotating tubular member 65 toward the distal direction is regulated. When the protrusion 106 abuts on the proximal side abutment portion 109, the movement of the rotating tubular member 65 toward the proximal direction is regulated. That is, the distal side abutment portion 108 and the proximal side abutment portion 109 serve as a movement range regulating portion which is configured to regulate the movement range of the rotating tubular member 65 in the directions parallel to the longitudinal axis C. The distal side abutment portion 108 and the proximal side abutment portion 109 regulate the movement range of the rotating tubular member 65 in the directions parallel to the longitudinal axis C so that the distal side seal ring 103 and the proximal side seal ring 105 come into contact with the inner peripheral portion of the rotating tubular member 65.

As shown in FIG. 3A and to FIG. 5, support members 111A and 111B are provided between the distal side seal ring 103 and the proximal side seal ring 105 in the directions parallel to the longitudinal axis C. The support member 111A is located to the distal direction side of the protrusion 106, and the support member 111B is located to the proximal direction side of the protrusion 106. The support members 111A and 111B extend in parts other than the opening 69 of the driving unit placement cavity 68 along the directions around the longitudinal axis. The support members 111A and 111B are provided coaxially with the longitudinal axis C, and support the rotating tubular member 65 with locating between the base member 57 and the rotating tubular member 65 in diametrical directions.

In a section perpendicular to the longitudinal axis C which passes through the support member 111A, a first diametrical dimension D1 from the longitudinal axis C to the inner peripheral portion of the support member 111A corresponds to a second diametrical dimension D2 from the longitudinal axis C to the outer peripheral portion of the base member 57. In the section perpendicular to the longitudinal axis C which passes through the support member 111A, a third diametrical dimension D3 from the longitudinal axis C to the outer peripheral portion of the support member 111A corresponds to a fourth diametrical dimension D4 from the longitudinal axis C to the inner peripheral portion of the rotating tubular member 65. The same applies to a section perpendicular to the longitudinal axis C which passes through the support member 111B. Thus, the position of the axial center of the rotating tubular member 65 is regulated by the support members 111A and 111B so that the rotating tubular member 65 is coaxial with the longitudinal axis C. That is, the support members 111A and 111B serve as an axial center position regulating portion which is configured to regulate the position of the axial center of the rotating tubular member 65 so that the rotating tubular member 65 is coaxial with the longitudinal axis C. As a result, the rotating tubular member 65 is kept coaxial with the longitudinal axis C even if an external force is applied to the rotating tubular member 65.

As shown in FIG. 3A, a ring abutment portion 112 on which the distal side seal ring 103 can abut is provided to the distal direction side of the distal side seal ring 103. A ring abutment portion 113 on which the distal side seal ring 103 can abut is provided to the proximal direction side of the distal side seal ring 103. The ring abutment portion 112 is formed on (in) the intermediary member 55, and the ring abutment portion 113 is formed on (in) the frame member 76 and the support member 111A. Therefore, the ring abutment portions 112 and 113 are provided to be fixed to the base member 57. When the distal side seal ring 103 abuts on the ring abutment portion 112, the movement of the distal side seal ring 103 toward the distal direction is regulated. When the distal side seal ring 103 abuts on the ring abutment portion 113, the movement of the distal side seal ring 103 toward the proximal direction is regulated. That is, the ring abutment portions 112 and 113 serve as a distal side movement regulating portion which is configured to regulate the movement of the distal side seal ring 103 in the directions parallel to the longitudinal axis C.

A ring abutment portion 115 on which the proximal side seal ring 105 can abut is provided to the distal direction side of the proximal side seal ring 105. A ring abutment portion 116 on which the proximal side seal ring 105 can abut is provided to the proximal direction side of the proximal side seal ring 105. The ring abutment portion 115 is formed on (in) the frame member 76 and the support member 111A, and the ring abutment portion 116 is formed on (in) the base member 57. Therefore, the ring abutment portions 115 and 116 are provided to be integral with or fixed to the base member 57. When the proximal side seal ring 105 abuts on the ring abutment portion 115, the movement of the proximal side seal ring 105 toward the distal direction is regulated. When the proximal side seal ring 105 abuts on the ring abutment portion, the movement of the proximal side seal ring 105 toward the proximal direction is regulated. That is, the ring abutment portions 115 and 116 serve as a proximal side movement regulating portion which is configured to regulate the movement of the proximal side seal ring 105 in the directions parallel to the longitudinal axis C.

Now, the function of the endoscope device 1 according to the present embodiment is described. When the insertion section 2 to which the rotating tubular member 65 and the tube member 30 are attached is inserted into a body and the rotating tubular member 65 and the tube member 30 are rotated relative to the insertion section 2 in one of the directions around the longitudinal axis, the motor 93 is driven by the operation in the driving operation input section 15. As a result, the driving shaft 96 rotates around the gear axis G1. The driving force from the motor 93 is then transmitted to the driving unit 70 via the driving shaft 96, and the driving unit 70 is driven. When the driving unit 70 is driven, the rotation driving force is transmitted to the inner peripheral gear portion 98, and the rotating tubular member 65 and the tube member 30 rotate together relative to the insertion section 2 in one of the directions around the longitudinal axis.

In this case, the movement range of the rotating tubular member 65 in the directions parallel to the longitudinal axis C is regulated by the distal side abutment portion 108 and the proximal side abutment portion 109. As a result, the movement range of the rotating tubular member 65 in the directions parallel to the longitudinal axis C is regulated so that the distal side seal ring 103 and the proximal side seal ring 105 come into contact with the inner peripheral portion of the rotating tubular member 65. Moreover, the position of the axial center of the rotating tubular member 65 is regulated by the support members 111A and 111B so that the rotating tubular member 65 is coaxial with the longitudinal axis C. As a result, the rotating tubular member 65 is kept (maintained) coaxial with the longitudinal axis C even if an external force is applied to the rotating tubular member 65. The movement range of the rotating tubular member 65 is regulated in the directions parallel to the longitudinal axis C, and the rotating tubular member 65 is kept coaxial with the longitudinal axis C. This ensures the performance of the rotation of the rotating tubular member 65 relative to the insertion section 2.

The distal side seal ring 103 which is the distal side ring member is provided on the distal side circular surface 101 of the base member 57, and the proximal side seal ring 105 which is the proximal side ring member is provided on the proximal side circular surface 102 of the base member 57. That is, the distal side seal ring 103 and the proximal side seal ring 105 are provided on the outer peripheral portion of the base member 57 which is formed into integral one from a single member. The distal side circular surface 101 is formed into the shape of a circular surface around the longitudinal axis C, and the proximal side circular surface 102 is formed into the shape of a circular surface around the longitudinal axis C. As described above, the movement range of the rotating tubular member 65 in the directions parallel to the longitudinal axis C is regulated by the distal side abutment portion 108 and the proximal side abutment portion 109 so that the distal side seal ring 103 and the proximal side seal ring 105 come into contact with the inner peripheral portion of the rotating tubular member 65. The position of the axial center of the rotating tubular member 65 is regulated by the support members 111A and 111B so that the rotating tubular member 65 is coaxial with the longitudinal axis C. This ensures that the distal side seal ring 103 maintains the liquid-tightness between the distal side circular surface 101 and the inner peripheral portion of the rotating tubular member 65 even if an external force is applied. Similarly, the proximal side seal ring 105 maintains the liquid-tightness between the proximal side circular surface 102 and the inner peripheral portion of the rotating tubular member 65 even if external force is applied. This effectively prevents liquid inflow from the outside of the insertion section 2 into the driving unit placement cavity 68.

In the endoscope device 1, the movement of the distal side seal ring 103 in the directions parallel to the longitudinal axis C is regulated by the ring abutment portions 112 and 113. The movement of the proximal side seal ring 105 in the directions parallel to the longitudinal axis C is regulated by the ring abutment portions 115 and 116. The regulation of the movement of the distal side seal ring 103 further ensures that the liquid-tightness between the distal side circular surface 101 and the inner peripheral portion of the rotating tubular member 65 is maintained. Similarly, the regulation of the movement of the proximal side seal ring 105 further ensures that the liquid-tightness between the proximal side circular surface 102 and the inner peripheral portion of the rotating tubular member 65 is maintained. This more effectively prevents liquid inflow from the outside of the insertion section 2 into the driving unit placement cavity 68.

FIG. 9 is a diagram showing the configuration of the second intermediary connection section 27 when the driving shaft 96 is not connected to the driving unit 70. As shown in FIG. 9, each of the distal side seal ring 103, the proximal side seal ring 105, the rotating tubular member 65, and the support members 111A and 111B is disposed at the corresponding position on the base member 57 while the driving shaft 96 is not connected to the driving unit 70. In this case, each of the proximal side seal ring 105, the support member 111B, the rotating tubular member 65, the support member 111A, and the distal side seal ring 103 is disposed at the corresponding position on the base member 57 from the distal direction side in this order. Here, when the driving shaft 96 is not connected to the driving unit 70, the driving unit 70 and the frame member 76 are located to the (more) inner peripheral direction side compared with when the driving shaft 96 is connected to the driving unit 70 (see FIG. 3A). Thus, when the driving shaft 96 is not connected to the driving unit 70, the rotating tubular member 65 does not abut on the distal side abutment portion 108 and the proximal side abutment portion 109, and thereby the movement range of the rotating tubular member 65 in the directions parallel to the longitudinal axis C is not regulated. Therefore, even after the rotating tubular member 65 is disposed at the corresponding position, the support member 111A and the distal side seal ring 103 can be easily disposed at the corresponding positions on the base member 57, respectively.

While the distal side seal ring 103, the proximal side seal ring 105, the rotating tubular member 65, and the support members 111A and 111B are respectively disposed at the corresponding positions on the base member 57, the distal end of the driving shaft 96 is connected to the driving unit 70. As a result, the driving unit 70 and the frame member 76 move toward the outer peripheral direction, and the rotating tubular member 65 can abut on the distal side abutment portion 108 and the proximal side abutment portion 109. Therefore, the movement range of the rotating tubular member 65 in the directions parallel to the longitudinal axis C is regulated. The movement range of the rotating tubular member 65 is regulated while the distal side seal ring 103 is disposed on the distal side circular surface 101 (the corresponding position) of the base member 57. Consequently, the distal side seal ring 103 ensures the liquid-tightness between the distal side circular surface 101 and the inner peripheral portion of the rotating tubular member 65. Similarly, the movement range of the rotating tubular member 65 is regulated while the proximal side seal ring 105 is disposed on the proximal side circular surface 102 (the corresponding position) of the base member 57. Consequently, the proximal side seal ring 105 ensures the liquid-tightness between the proximal side circular surface 102 and the inner peripheral portion of the rotating tubular member 65. As described above, according to the present embodiment, the rotating tubular member 65 is easily attached to the insertion section 2.

Accordingly, the endoscope device 1 which is the insertion device having the configuration described above provides the following advantageous effects. That is, in the endoscope device 1, the distal side seal ring 103 which is the distal side ring member is provided on the distal side circular surface 101 of the base member 57, and the proximal side seal ring 105 which is the proximal side ring member is provided on the proximal side circular surface 102 of the base member 57. That is, the distal side seal ring 103 and the proximal side seal ring 105 are provided on the outer peripheral portion of the base member 57 which is formed into integral one from a single member. The distal side circular surface 101 is formed into the shape of a circular surface around the longitudinal axis C, and the proximal side circular surface 102 is formed into the shape of a circular surface around the longitudinal axis C. The movement range of the rotating tubular member 65 in the directions parallel to the longitudinal axis C is regulated by the distal side abutment portion 108 and the proximal side abutment portion 109 so that the distal side seal ring 103 and the proximal side seal ring 105 come into contact with the inner peripheral portion of the rotating tubular member 65. The position of the axial center of the rotating tubular member 65 is regulated by the support members 111A and 111B so that the rotating tubular member 65 is coaxial with the longitudinal axis C. This configuration can ensure the performance of the rotation of the rotating tubular member 65 relative to the insertion section 2. This configuration also ensures that the distal side seal ring 103 maintains the liquid-tightness between the distal side circular surface 101 and the inner peripheral portion of the rotating tubular member 65 even if external force is applied. Similarly, this configuration ensures that the proximal side seal ring 105 maintains the liquid-tightness between the proximal side circular surface 102 and the inner peripheral portion of the rotating tubular member 65 even if external force is applied. This can effectively prevent liquid inflow from the outside of the insertion section 2 into the driving unit placement cavity 68.

(Modifications)

In the first embodiment, the inner peripheral gear portion 98 is provided in the protrusion 106, and the protrusion 106 is provided integrally with the rotating tubular member 65. However, the present invention is not limited to this. Moreover, in the first embodiment, the distal side abutment portion 108 and the proximal side abutment portion 109 are provided on (in) the frame member 76 to which the driving unit 70 is attached. However, the present invention is not limited to this. For example, as in a first modification shown in FIG. 10, the protrusion 106 may be formed in (by) a pin member 121 fixed to the rotating tubular member 65. In the present modification as well, the protrusion 106 projects toward the inner peripheral direction between the distal side seal ring 103 and the proximal side seal ring 105 in the directions parallel to the longitudinal axis C.

In the present modification, a slot portion 122 is provided in the outer circumferential portion of the base member 57. The slot portion (groove portion) 122 is located between the distal side seal ring 103 and the proximal side seal ring 105 in the directions parallel to the longitudinal axis C, and is located to the proximal direction side of the opening 69 of the driving unit placement cavity 68. The distal side abutment portion 108 and the proximal side abutment portion 109 are provided in the slot portion 122. That is, the distal side abutment portion 108 and the proximal side abutment portion 109 are formed integrally with the base member 57. In the present modification, the movement of the rotating tubular member 65 toward the proximal direction is regulated when the protrusion 106 abuts on the distal side abutment portion 108, as in the first embodiment. When the protrusion 106 abuts on the proximal side abutment portion 109, the movement of the rotating tubular member 65 toward the proximal direction is regulated. Therefore, in the present modification as well, the distal side abutment portion 108 and the proximal side abutment portion 109 are configured to regulate the movement range of the rotating tubular member 65 in the directions parallel to the longitudinal axis C so that the distal side seal ring 103 and the proximal side seal ring 105 come into contact with the inner peripheral portion of the rotating tubular member 65.

As described above, according to the first modification, the protrusion 106 has only to be provided to be integral with or fixed to the rotating tubular member 65. The protrusion 106 has only to be formed to project toward the inner peripheral direction between the distal side seal ring (distal side ring member) 103 and the proximal side seal ring (proximal side ring member) 105 in the directions parallel to the longitudinal axis C. The distal side abutment portion 108 and the proximal side abutment portion 109 have only to be provided to be integral with or fixed to the base member 57. The movement of the rotating tubular member 65 toward the distal direction has only to be regulated when the protrusion 106 abuts on the distal side abutment portion 108. Similarly, the movement of the rotating tubular member 65 toward the proximal direction has only to be regulated when the protrusion 106 abuts on the proximal side abutment portion 109. In this configuration, the distal side abutment portion 108 and the proximal side abutment portion 109 are configured to regulate the movement range of the rotating tubular member 65 in the directions parallel to the longitudinal axis C so that the distal side seal ring 103 and the proximal side seal ring 105 come into contact with the inner peripheral portion of the rotating tubular member 65.

Although the two support members 111A and 111B are provided in the first embodiment, the present invention is not limited to this. For example, as in a second modification shown in FIG. 11 and FIG. 12, only one support member 111 may be provided. In the present modification, a position of the support member 111 coincides with (corresponds to) a position of the protrusion 106 in the directions parallel to the longitudinal axis C. Therefore, the support member 111 is located between the distal side seal ring 103 and the proximal side seal ring 105 in the directions parallel to the longitudinal axis C. As in the first embodiment, the support member 111 extends in parts other than the opening 69 of the driving unit placement cavity 68 along the directions around the longitudinal axis. In the present modification as well, the support member 111 is provided coaxially with the longitudinal axis C, and supports the rotating tubular member 65 between the base member 57 and the rotating tubular member 65 in the diametrical directions.

As in the first embodiment, in a section perpendicular to the longitudinal axis C which passes through the support member 111, the first diametrical dimension D1 from the longitudinal axis C to the inner peripheral portion of the support member 111 corresponds to (coincides with) the second diametrical dimension D2 from the longitudinal axis C to the outer peripheral portion of the base member 57. In the section perpendicular to the longitudinal axis C which passes through the support member 111, the third diametrical dimension D3 from the longitudinal axis C to the outer peripheral portion of the support member 111 corresponds to the fourth diametrical dimension D4 from the longitudinal axis C to the inner peripheral portion of the rotating tubular member 65. Thus, the position of the axial center of the rotating tubular member 65 is regulated by the support member 111 so that the rotating tubular member 65 is coaxial with the longitudinal axis C. As a result, the rotating tubular member 65 is kept (maintained) coaxial with the longitudinal axis C even if external force is applied to the rotating tubular member 65.

As described above, according to the second modification, the support member (111; 111A, 111B) has only to be provided coaxially with the longitudinal axis C between the distal side seal ring (distal side ring member) 103 and the proximal side seal ring (proximal side ring member) 105 in the directions parallel to the longitudinal axis C. The support member (111; 111A, 111B) has only to support the rotating tubular member 65 between the base member 57 and the rotating tubular member 65 in the diametrical directions. In the section perpendicular to the longitudinal axis C which passes through the support member (111; 111A, 111B), the first diametrical dimension D1 from the longitudinal axis C to the inner peripheral portion of the support member (111; 111A, 111B) has only to correspond to the second diametrical dimension D2 from the longitudinal axis C to the outer peripheral portion of the base member 57. Similarly, the third diametrical dimension D3 from the longitudinal axis C to the outer peripheral portion of the support member (111; 111A, 111B) has only to correspond to the fourth diametrical dimension D4 from the longitudinal axis C to the inner peripheral portion of the rotating tubular member 65. In this configuration, the position of the axial center of the rotating tubular member 65 is regulated by the support member (111; 111A, 111B) so that the rotating tubular member 65 is coaxial with the longitudinal axis C.

In the first embodiment, the ring abutment portion 112 is formed in (on) the intermediary member 55, and the ring abutment portion 113 is formed in (on) the frame member 76 and the support member 111A. However, the present invention is not limited to this. Similarly, the ring abutment portion 115 is formed in (on) the frame member 76 and the support member 111B, and the ring abutment portion 116 is formed in (on) the base member 57. However, the present invention is not limited to this. That is, the distal side movement regulating portion (112, 113) and the proximal side movement regulating portion (115, 116) have only to be provided to be integral with or fixed to the base member 57. The movement of the distal side seal ring 103 in the directions parallel to the longitudinal axis C has only to be regulated by the distal side movement regulating portion (112, 113). Similarly, the movement of the proximal side seal ring 105 in the directions parallel to the longitudinal axis C has only to be regulated by the proximal side movement regulating portion (115, 116).

Although the insertion device is the endoscope device 1 in the first embodiment, the present invention is not limited to this. For example, in a manipulator device which is the insertion device, the rotating tubular member 65 may be attached to a manipulator insertion section. That is, the insertion device has only to include an insertion section extending along the longitudinal axis C, and the insertion section has only to be an insertion section which is configured to be inserted into, for example, a body.

It is appreciated from the above that the endoscope device (1) has only to include the base member 57 which is formed into integral one from a single member. The base member 57 has only to include the cavity defining portion 67 defining the driving unit placement cavity 68 in which the driving unit 70 is disposed and which is open to the outside of the insertion section 2 through the opening 69, the distal side circular surface 101 which is provided to the distal direction side of the opening 69 of the driving unit placement cavity 68 and which is formed into the shape of a circular surface around the longitudinal axis C on the outer peripheral portion of the base member 57, and the proximal side circular surface 102 which is provided to the proximal direction side of the opening 69 of the driving unit placement cavity 68 and which is formed into the shape of a circular surface around the longitudinal axis C on the outer peripheral portion of the base member 57. The distal side ring member (103) has only to be provided on the distal side circular surface 101 to maintain the liquid-tightness between the distal side circular surface 101 and the inner peripheral portion of the rotating tubular member 65. The proximal side ring member (105) has only to be provided on the proximal side circular surface 102 to maintain the liquid-tightness between the proximal side circular surface 102 and the inner peripheral portion of the rotating tubular member 65. The endoscope device (1) has only to include the movement range regulating portion (108, 109) which is configured to regulate the movement range of the rotating tubular member 65 in the directions parallel to the longitudinal axis C so that the distal side ring member (103) and the proximal side ring member (105) come into contact with the inner peripheral portion of the rotating tubular member 65. The endoscope device (1) has only to include the axial center position regulating portion (111; 111A, 111B) which is configured to regulate the position of the axial center of the rotating tubular member 65 so that the rotating tubular member 65 is coaxial with the longitudinal axis C.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion device comprising:
an insertion section which extends along a longitudinal axis with the longitudinal axis being an axial center;
a rotating tubular member which is disposed to cover an outer peripheral of the insertion section;
a driving unit which is configured to be driven to rotate the rotating tubular member relative to the insertion section in one of directions around the longitudinal axis;
a base member which is integrally formed in a part of the insertion section, and which defines a driving unit placement cavity to dispose the driving unit, the driving unit placement cavity being opened to an outside of the insertion section, an opening of the driving unit placement cavity being formed on an outer peripheral surface of the base member;
a support member which is disposed between the base member and the rotating tubular member, the support member being configured to abut on an outer peripheral portion of the base member and an inner peripheral portion of the rotating tubular member, a dimension of the support member in a direction along the longitudinal axis being smaller than a dimension of each of the base member and the rotating tubular member in the direction along the longitudinal axis, a space being formed between the outer peripheral portion of the base member and the inner peripheral portion of the rotating tubular member and in a region adjacent to the support member in the direction along the longitudinal axis, the driving unit being engaged with the inner peripheral portion of the rotating tubular member in the space so that a rotation driving force is transmittable from the driving unit to the rotating tubular member, the support member being fixed to the base member, a cross-sectional shape of the support member perpendicular to the longitudinal axis being a C-shape, the support member extending along the directions around the longitudinal axis, the C-shaped support member extending in an entire region other than the opening of the driving unit placement cavity in the directions around the longitudinal axis, the support member being configured to support the rotating tubular member so that a rotation axis of the rotating tubular member is aligned with the longitudinal axis of the insertion section when the rotating tubular member rotates, and thereby being configured to hold the rotating tubular member at a position where the rotation driving force is transmittable from the driving unit to the inner peripheral portion of the rotating tubular member;
a distal side ring member which is provided in the space between the outer peripheral portion of the base member and the inner peripheral portion of the rotating tubular member and in a region apart from the support member toward a distal direction, and which is a separated body from the support member, the distal side ring member being configured to maintain liquid-tightness between the outer peripheral portion of the base member and the inner peripheral portion of the rotating tubular member in a part to a distal direction side of the driving unit placement cavity in the space, and thereby being configured to prevent liquid inflow from the distal direction side into the driving unit placement cavity; and
a proximal side ring member which is provided in the space between the outer peripheral portion of the base member and the inner peripheral portion of the rotating tubular member and in a region apart from the support member toward a proximal direction, and which is a separated body from the support member, the distal side ring member being configured to maintain liquid-tightness between the outer peripheral portion of the base member and the inner peripheral portion of the rotating tubular member in a part to a proximal direction side of the driving unit placement cavity in the space, and thereby being configured to prevent liquid inflow from the proximal direction side into the driving unit placement cavity.

2. The insertion device according to claim 1, wherein the support member configured to regulate a position of the rotation axis of the rotating tubular member so that the rotation axis is coaxial with the longitudinal axis.

3. The insertion device according to claim 2, further comprising a movement range regulating portion which is configured to regulate the movement range of the rotating tubular member in directions parallel to the longitudinal axis so that the distal side ring member and the proximal side ring member come into contact with the inner peripheral portion of the rotating tubular member.

4. The insertion device according to claim 3, further comprising a linear member extending through an inside of the insertion section along the longitudinal axis,
    wherein the linear member is connected to the driving unit, and the driving unit is configured to be driven when a driving force is transmitted to the driving unit via the linear member.

5. The insertion device according to claim 4, wherein the base member includes
    a distal side circular surface which is formed into the shape of a circular surface around the longitudinal axis on the outer peripheral portion of the base member in a part to the distal direction side of the driving unit placement cavity, and
    a proximal side circular surface which is formed into the shape of a circular surface around the longitudinal axis on the outer peripheral portion of the base member in a part to the proximal direction side of the driving unit placement cavity.

6. The insertion device according to claim 5, wherein the movement range regulating portion includes
    a protrusion which is provided to be integral with or fixed to the rotating tubular member, and which is formed to project toward an inner peripheral direction between the distal side ring member and the proximal side ring member in the directions parallel to the longitudinal axis,
    a distal side abutment portion which is provided to be integral with or fixed to the base member, and which is configured to regulate a movement of the rotating tubular member toward the distal direction when the protrusion abuts on the distal side abutment portion, and
    a proximal side abutment portion which is provided to be integral with or fixed to the base member, and which is configured to regulate a movement of the rotating tubular member toward the proximal direction when the protrusion abuts on the proximal side abutment portion.

7. The insertion device according to claim 6, wherein the protrusion includes a driving force receiving portion which is connected to the driving unit, and to which the rotation driving force to rotate the rotating tubular member is configured to be transmitted when the driving unit is driven.

8. The insertion device according to claim 7, further comprising a frame member which is provided in the driving unit placement cavity to be fixed to the base member, and to which the driving unit is attached,
    wherein the driving unit includes a gear which is configured to be driven and thereby configured to be rotated around a gear axis,
    the driving force receiving portion includes an inner peripheral gear portion which is toothed with the gear, and
    the distal side abutment portion and the proximal side abutment portion are provided in the frame member.

9. The insertion device according to claim 5, wherein the support member is provided coaxially with the longitudinal axis between the distal side ring member and the proximal side ring member in the directions parallel to the longitudinal axis,
    in a section perpendicular to the longitudinal axis which passes through the support member, a first diametrical dimension from the longitudinal axis to an inner peripheral portion of the support member corresponds to a second diametrical dimension from the longitudinal axis to the outer peripheral portion of the base member, and
    a third diametrical dimension from the longitudinal axis to an outer peripheral portion of the support member corresponds to a fourth diametrical dimension from the longitudinal axis to the inner peripheral portion of the rotating tubular member.

10. The insertion device according to claim 9, further comprising
    a distal side movement regulating portion which is provided to be integral with or fixed to the base member, and which is configured to regulate a movement of the distal side ring member in the directions parallel to the longitudinal axis, and
    a proximal side movement regulating portion which is provided to be integral with or fixed to the base member, and which is configured to regulate a movement of the proximal side ring member in the directions parallel to the longitudinal axis.

11. The insertion device according to claim 1, wherein the insertion section is an endoscope insertion section, and
    the endoscope insertion section includes an image pickup element provided in a distal portion thereof and configured to image a subject.

12. The insertion device according to claim 1, further comprising
    a tube member which is attached to the rotating tubular member so that the insertion section is inserted through the tube member, and which is rotatable relative to the insertion section in the directions around the longitudinal axis together with the rotating tubular member,
    wherein the tube member includes a fin spirally extending along the longitudinal axis.

13. A rotating tubular member in an insertion device, the insertion device including an insertion section which extends along a longitudinal axis with the longitudinal axis being an axial center, and a driving unit which is configured to be driven, the rotating tubular member being disposed to cover an outer peripheral of the insertion section and being configured to rotate relative to the insertion section in one of directions around the longitudinal axis when the driving unit is driven,
    wherein the rotating tubular member is attached to the insertion section in which a base member is integrally formed, the base member defining a driving unit placement cavity to dispose the driving unit, the driving unit placement cavity being opened to an outside of the insertion section, an opening of the driving unit placement cavity being formed on an outer peripheral surface of the base member,
    the rotating tubular member is configured to be supported by a support member, the support member being disposed between the base member and the rotating tubular member, the support member being configured to abut on an outer peripheral portion of the base member and an inner peripheral portion of the rotating tubular member, a dimension of the support member in a direction along the longitudinal axis being smaller than a dimension of each of the base member and the rotating tubular member in the direction along the longitudinal axis, a space being formed between the outer peripheral portion of the base member and the inner peripheral portion of the rotating tubular member and in a region adjacent to the support member in the direction along the longitudinal axis, the driving unit being engaged with the inner peripheral portion of the rotating tubular member in the space so that a rotation driving force is transmittable from the driving unit to the rotating tubular member, the support member being fixed to the base member, a cross-sectional shape of the support member perpendicular to the longitudinal axis being a C-shape, the support member extending along the directions around the longitudinal axis, the C-shaped support member extending in an entire region other than the opening of the driving unit placement cavity in the directions around the longitudinal axis, the support member being configured to support the rotating tubular member so that a rotation axis of the rotating tubular member is aligned with the longitudinal axis of the insertion section when the rotating tubular member rotates, and thereby being configured to hold the rotating tubular member at a position where the rotation driving force is transmittable from the driving unit to the inner peripheral portion of the rotating tubular member, liquid inflow from the distal direction side into the driving unit placement cavity is prevented by a distal side ring member, the distal side ring member being provided in the space between the outer peripheral portion of the base member and the inner peripheral portion of the rotating tubular member and in a region apart from the support member toward a distal direction, the distal side ring member being a separated body from the support member, the distal side ring member being configured to maintain liquid-tightness between the outer peripheral portion of the base member and the inner peripheral portion of the rotating tubular member in a part to a distal direction side of the driving unit placement cavity in the space, and liquid inflow from the proximal direction side into the driving unit placement cavity is prevented by a proximal side ring member, the proximal side ring member being provided in the space between the outer peripheral portion of the base member and the inner peripheral portion of the rotating tubular member and in a region apart from the support member toward a proximal direction, the proximal side ring member being a separated body from the support member, the proximal side ring member being configured to maintain liquid-tightness between the outer peripheral portion of the base member and the inner peripheral portion of the rotating tubular member in a part to a proximal direction side of the driving unit placement cavity in the space.

* * * * *